(12) United States Patent
Scarpine et al.

(10) Patent No.: US 10,874,410 B2
(45) Date of Patent: Dec. 29, 2020

(54) CLOT REMOVAL BY ADHESION

(71) Applicant: Covidien LP, Mansfield, MA (US)

(72) Inventors: Frank Scarpine, Brea, CA (US); Rick Williams, Laguna Niguel, CA (US); Francis Bernard, Dana Point, CA (US); Maria de Jesus Sanson, San Clemente, CA (US)

(73) Assignee: COVIDIEN LP, Mansfield, MA (US)

( * ) Notice: Subject to any disclaimer, the term of this patent is extended or adjusted under 35 U.S.C. 154(b) by 199 days.

(21) Appl. No.: 14/932,433

(22) Filed: Nov. 4, 2015

(65) Prior Publication Data

US 2017/0119407 A1    May 4, 2017

(51) Int. Cl.
*A61B 17/22* (2006.01)
*A61M 1/00* (2006.01)
*A61B 17/30* (2006.01)

(52) U.S. Cl.
CPC ............. *A61B 17/22* (2013.01); *A61M 1/008* (2013.01); *A61B 2017/22034* (2013.01); *A61B 2017/308* (2013.01); *A61B 2217/005* (2013.01)

(58) Field of Classification Search
CPC .......... A61B 17/22; A61B 2017/22034; A61B 2017/308; A61M 1/008; A61M 25/007
See application file for complete search history.

(56) References Cited

U.S. PATENT DOCUMENTS

| | | |
|---|---|---|
| 4,795,447 A | 1/1989 | Dodson |
| 5,931,831 A | 8/1999 | Linder |
| 5,972,019 A | 10/1999 | Engelson et al. |
| 6,254,571 B1 * | 7/2001 | Hart ...................... A61B 17/221 604/107 |
| 7,449,010 B1 * | 11/2008 | Hayase ............. A61M 25/0054 604/93.01 |
| 7,914,549 B2 | 3/2011 | Morsi |
| 8,602,973 B2 | 12/2013 | Wendlandt |
| 8,603,014 B2 | 12/2013 | Alleman et al. |
| 8,837,800 B1 | 9/2014 | Bammer et al. |

(Continued)

FOREIGN PATENT DOCUMENTS

| | | |
|---|---|---|
| EP | 2319575 B1 | 11/2013 |
| GB | 2179258 A | 3/1987 |

(Continued)

*Primary Examiner* — Kathleen S Holwerda
*Assistant Examiner* — Brooke Labranche
(74) *Attorney, Agent, or Firm* — Fortem IP LLP; Mary Fox

(57) ABSTRACT

An aspiration catheter can be used to capture and retrieve vascular debris from blood vessels. The aspiration catheter can include a distal segment having ports positioned along its longitudinal length and about its circumference. The distal segment can capture thrombus at least partially on an exterior of the distal segment when aspiration is applied through the ports, and retrieve the thrombus when the elongate member is retracted proximally. The distal segment can be modified from a non-collapsed configuration to a collapsed configuration when aspiration is applied through the ports. The distal segment can have projections arranged along and around its circumference. The projections can be configured to slide distally through a thrombus within a blood vessel and to pull the thrombus when the elongate member is retracted proximally.

7 Claims, 5 Drawing Sheets

(56) References Cited

U.S. PATENT DOCUMENTS

| | | |
|---|---|---|
| 8,986,241 B2 | 3/2015 | Evans et al. |
| 9,119,656 B2 | 9/2015 | Bose et al. |
| 9,126,018 B1 | 9/2015 | Garrison |
| 9,211,132 B2 | 12/2015 | Bowman |
| 9,241,699 B1 | 1/2016 | Kume et al. |
| 9,265,512 B2 | 2/2016 | Garrison et al. |
| 9,308,007 B2 | 4/2016 | Cully et al. |
| 9,399,118 B2 | 7/2016 | Kume et al. |
| 9,445,828 B2 | 9/2016 | Turjman et al. |
| 9,445,829 B2 | 9/2016 | Brady et al. |
| 9,492,637 B2 | 11/2016 | Garrison et al. |
| 9,539,022 B2 | 1/2017 | Bowman |
| 9,561,345 B2 | 2/2017 | Garrison et al. |
| 9,579,119 B2 | 2/2017 | Cully et al. |
| 9,585,741 B2 | 3/2017 | Ma |
| 9,642,635 B2 | 5/2017 | Vale et al. |
| 9,655,633 B2 | 5/2017 | Leynov et al. |
| 9,737,318 B2 | 8/2017 | Monstadt et al. |
| 9,770,251 B2 | 9/2017 | Bowman et al. |
| 9,801,643 B2 | 10/2017 | Hansen et al. |
| 9,861,783 B2 | 1/2018 | Garrison et al. |
| 9,993,257 B2 | 6/2018 | Losordo et al. |
| 10,028,782 B2 | 7/2018 | Orion |
| 10,029,008 B2 | 7/2018 | Creighton |
| 10,039,906 B2 | 8/2018 | Kume et al. |
| 2008/0033423 A1 | 2/2008 | Peacock |
| 2009/0281564 A1 | 11/2009 | Kontos |
| 2010/0114093 A1 | 5/2010 | Mahapatra et al. |
| 2010/0152706 A1 | 6/2010 | Morris et al. |
| 2011/0112436 A1 | 5/2011 | Jones et al. |
| 2013/0030461 A1 | 1/2013 | Marks et al. |
| 2013/0110082 A1 | 5/2013 | Tekulve |
| 2013/0165944 A1 | 6/2013 | Gal et al. |
| 2013/0281788 A1 | 10/2013 | Garrison |
| 2014/0276074 A1 | 9/2014 | Warner |
| 2014/0343595 A1 | 11/2014 | Monstadt et al. |
| 2015/0133973 A1* | 5/2015 | Milner ............. A61B 17/3207 606/159 |
| 2015/0359547 A1 | 12/2015 | Vale et al. |
| 2016/0015402 A1 | 1/2016 | Brady et al. |
| 2016/0015935 A1 | 1/2016 | Chan et al. |
| 2016/0106448 A1 | 4/2016 | Brady et al. |
| 2016/0106449 A1 | 4/2016 | Brady et al. |
| 2016/0113663 A1 | 4/2016 | Brady et al. |
| 2016/0113665 A1 | 4/2016 | Brady et al. |
| 2016/0151618 A1 | 6/2016 | Powers et al. |
| 2016/0157985 A1 | 6/2016 | Vo et al. |
| 2016/0199620 A1 | 7/2016 | Pokorney et al. |
| 2016/0296690 A1 | 10/2016 | Kume et al. |
| 2016/0302808 A1 | 10/2016 | Loganathan et al. |
| 2016/0375180 A1 | 12/2016 | Anzai |
| 2017/0079766 A1 | 3/2017 | Wang et al. |
| 2017/0079767 A1 | 3/2017 | Leon-Yip |
| 2017/0086862 A1 | 3/2017 | Vale et al. |
| 2017/0100143 A1 | 4/2017 | Grandfield |
| 2017/0105743 A1 | 4/2017 | Vale et al. |
| 2017/0164963 A1 | 6/2017 | Goyal |
| 2017/0215902 A1 | 8/2017 | Leynov et al. |
| 2017/0224953 A1 | 8/2017 | Tran et al. |
| 2017/0281909 A1 | 10/2017 | Northrop et al. |
| 2017/0290599 A1 | 10/2017 | Youn et al. |
| 2018/0049762 A1 | 2/2018 | Seip et al. |
| 2018/0084982 A1 | 3/2018 | Yamashita et al. |
| 2018/0116717 A1 | 5/2018 | Taff et al. |
| 2018/0132876 A1 | 5/2018 | Zaidat |
| 2018/0140314 A1 | 5/2018 | Goyal et al. |
| 2018/0140315 A1 | 5/2018 | Bowman et al. |
| 2018/0140354 A1 | 5/2018 | Lam et al. |
| 2018/0185614 A1 | 7/2018 | Garrison et al. |

FOREIGN PATENT DOCUMENTS

| | | |
|---|---|---|
| JP | 2014004219 A | 1/2014 |
| JP | 2018118132 A | 8/2018 |
| KR | 20180102877 A | 9/2018 |
| WO | WO-2014/094341 A1 | 6/2014 |
| WO | WO-2014/094342 A1 | 6/2014 |
| WO | 2015141317 A1 | 9/2015 |
| WO | 2017192999 A1 | 11/2017 |
| WO | 2018019829 A1 | 2/2018 |
| WO | 2018033401 A1 | 2/2018 |
| WO | 2018046408 A2 | 3/2018 |
| WO | 2018137029 A1 | 8/2018 |
| WO | 2018137030 A1 | 8/2018 |
| WO | 2018145212 A1 | 8/2018 |
| WO | 2018156813 A1 | 8/2018 |
| WO | 2018172891 A1 | 9/2018 |
| WO | 2018187776 A1 | 10/2018 |

* cited by examiner

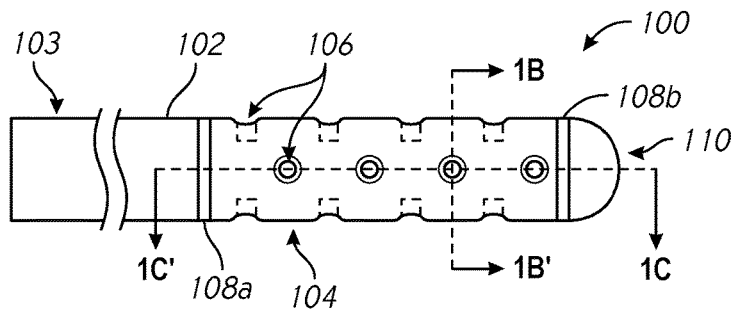
FIG. 1A
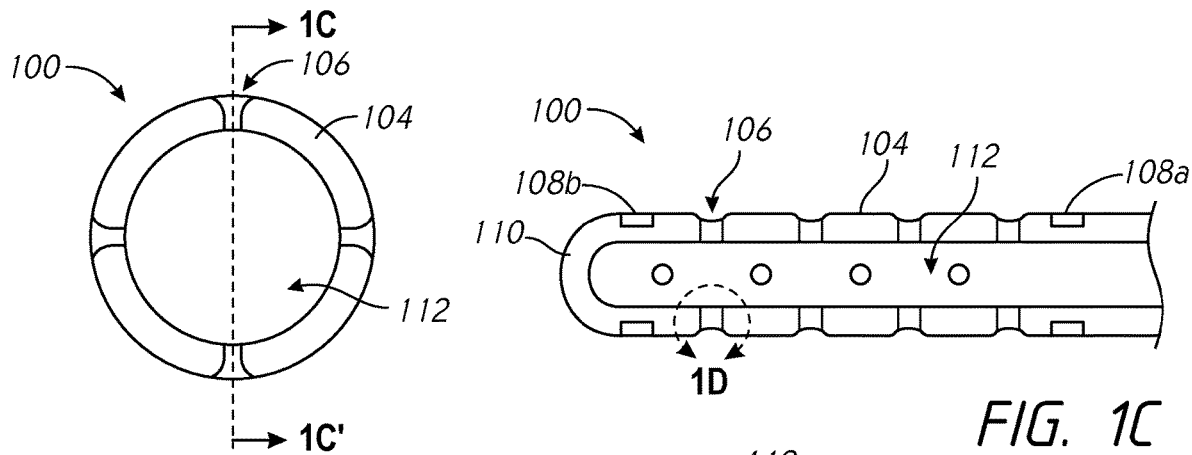
FIG. 1B
FIG. 1C
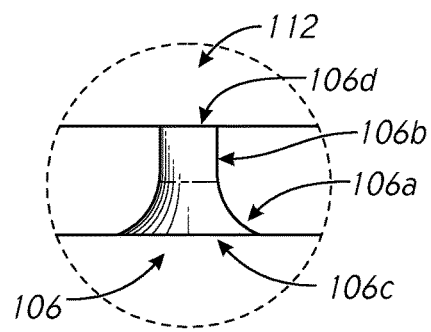
FIG. 1D

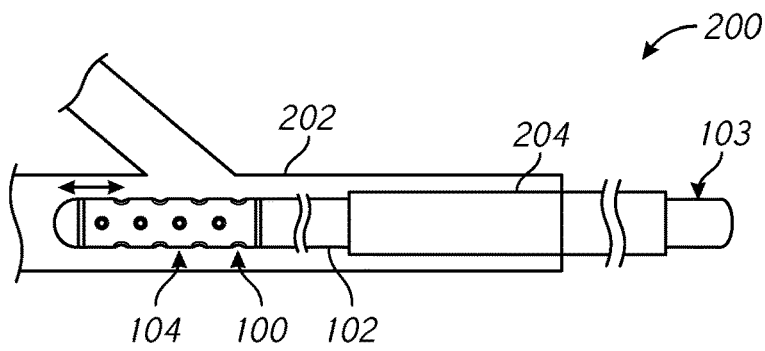
FIG. 2A
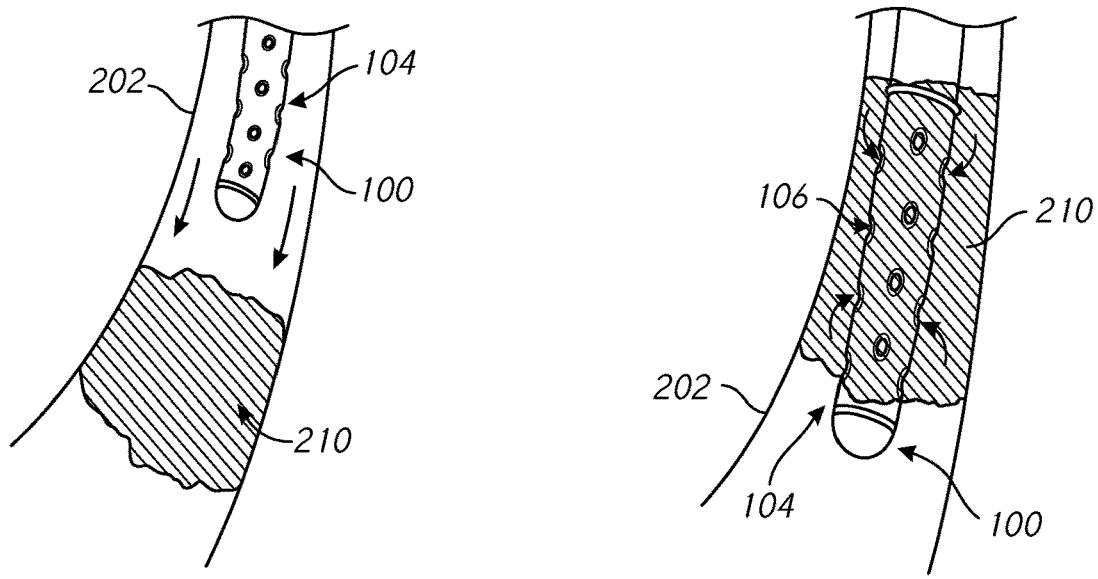
FIG. 2B
FIG. 2C
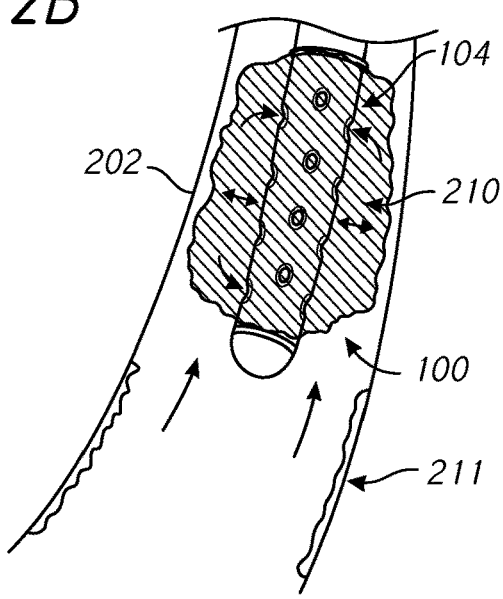
FIG. 2D

CLOT REMOVAL BY ADHESION

BACKGROUND

Blood vessels can become partially or completely occluded by vascular debris (e.g., thrombi, emboli) in a vasculature (e.g., blood vessel), thereby impeding or disrupting the flow of blood therethrough. For example, intracranial arteries can become occluded by thromboembolisms. Disruption of blood flow by the occlusion can prevent oxygen and nutrients from being delivered to tissues downstream of the occlusion. Deprivation of oxygen and nutrients to tissue distal to an occlusion can impair proper function of the tissue, and may result in cellular death. Cellular death increases with duration of the occlusion.

SUMMARY

A catheter can be used to capture and retrieve vascular debris from blood vessels. The catheter can include a distal segment having ports positioned along its longitudinal length and about its circumference. The distal segment can capture thrombus at least partially on an exterior of the distal segment when aspiration is applied through the ports, and retrieve the thrombus when the elongate member is retracted proximally.

The subject technology is illustrated, for example, according to various aspects described below. Various examples of aspects of the subject technology are described as numbered clauses (1, 2, 3, etc.) for convenience. These are provided as examples and do not limit the subject technology. It is noted that any of the dependent clauses may be combined in any combination, and placed into a respective independent clause, e.g., clause 1, clause 8, or clause 18. The other clauses can be presented in a similar manner.

Clause 1. A method for removing thrombus from a blood vessel, the method comprising:
positioning a distal segment of an aspiration catheter in a blood vessel, a distal end of the aspiration catheter being closed, the distal segment having an array of ports, the ports of the array positioned along a longitudinal length of the distal segment and about a circumference of the distal segment,
positioning the distal segment in contact with a thrombus in the blood vessel;
applying aspiration through the array of ports while the distal segment is in contact with the thrombus; and
withdrawing the aspiration catheter from the blood vessel with the thrombus at least partially on an exterior of the distal segment.

Clause 2. The method of clause 1, wherein the aspiration catheter is withdrawn from the blood vessel with a majority of the thrombus on the exterior of the distal segment.

Clause 3. The method of clause 1, wherein the distal segment has a collapsed configuration and a non-collapsed configuration, the distal segment being modified from the non-collapsed configuration to a collapsed configuration when aspiration is applied through a lumen of the catheter.

Clause 4. The method of clause 1, wherein positioning the distal segment in contact with the thrombus comprises positioning the distal segment through the thrombus, the distal segment positioned with at least a portion of the array of ports being in the thrombus.

Clause 5. The method of clause 1, wherein withdrawing the aspiration catheter from the blood vessel comprises retracting the aspiration catheter into an additional catheter with the thrombus at least partially on an exterior of the distal segment.

Clause 6. The method of clause 5, wherein withdrawing the aspiration catheter from the blood vessel comprises withdrawing the aspiration catheter a distance within the blood vessel outside the additional catheter before retracting the aspiration catheter into the additional catheter.

Clause 7. The method of clause 1, further comprising engaging the thrombus with at least one radially outwardly protruding member of the aspiration catheter.

Clause 8. An aspiration catheter comprising:
an elongate member comprising a distal end, a distal segment, and a lumen extending to the distal segment, the distal end being closed, the distal segment comprising an array of ports positioned along a longitudinal length of the distal segment and about a circumference of the distal segment, the array of ports being in fluid communication with the lumen, at least a portion of the distal segment that includes at least some of the array of ports being collapsible when aspiration is applied through the lumen.

Clause 9. The aspiration catheter of clause 8, wherein the array of ports are configured to inhibit movement of thrombus into the lumen when aspiration is applied through the lumen to the ports.

Clause 10. The aspiration catheter of clause 8, wherein the distal end has a rounded shape.

Clause 11. The aspiration catheter of clause 8, wherein the array of ports are spaced evenly around a longitudinal axis of the distal segment.

Clause 12. The aspiration catheter of clause 8, wherein each port of the array of ports has an inner opening that is smaller than an outer opening of the port.

Clause 13. The aspiration catheter of clause 8, wherein the distal segment comprises a tubular body and one or more projections disposed along and around the tubular body, the one or more projections projecting radially outwardly from the tubular body.

Clause 14. The aspiration catheter of clause 13, wherein each of the one or more projection projections is configured to slide distally through a thrombus within a blood vessel and to pull the thrombus when the elongate member is retracted proximally.

Clause 15. The aspiration catheter of clause 14, wherein each of the one or more projections comprises a distal surface and a proximal surface, the distal surface and the proximal surface each having a slope relative to a longitudinal axis of the distal segment, and the slope of the distal surface being less than the slope of the proximal surface.

Clause 16. The aspiration catheter of clause 13, wherein at least one projection spirals along and around the distal segment of the elongate member.

Clause 17. The aspiration catheter of clause 16, wherein each spiraling projection comprises a distal surface and a proximal surface, the distal surface and the proximal surface each having a slope relative to a longitudinal axis of the distal segment, the slope of the distal surface being less than the slope of the proximal surface.

Clause 18. An aspiration catheter, comprising:
an elongate member comprising a distal end, a distal segment, and a lumen extending to the distal segment, the distal end being closed, the distal segment comprising an array of ports positioned along a longitudinal length of the distal segment and about a circumference of the distal segment, the array of ports being in fluid communication with the lumen; and a set of projections disposed along and around the distal segment, each projection of the set of projections projecting radially outwardly from the elongate member.

Clause 19. The aspiration catheter of clause 18, wherein at least a portion of the distal segment that includes at least some of the array of ports being collapsible when aspiration is applied through the lumen.

Clause 20. The aspiration catheter of clause 18, wherein the set of projections comprises a plurality of projections equally spaced and arranged around a longitudinal axis of the distal segment.

Clause 21. The aspiration catheter of clause 18, wherein each projection of the plurality of projections is configured to slide distally through a thrombus within a blood vessel and to pull the thrombus when the elongate member is retracted proximally.

Clause 22. The aspiration catheter of clause 21, wherein each projection of the plurality of projections comprises a distal surface and a proximal surface, the distal surface and the proximal surface each having a slope relative to a longitudinal axis of the distal segment, the slope of the distal surface being less than the slope of the proximal surface.

Clause 23. The aspiration catheter of clause 18, wherein the set of projections comprises one or more ridges spiraling around a longitudinal axis of the distal segment.

Additional features and advantages of the subject technology will be set forth in the description below, and in part will be apparent from the description, or may be learned by practice of the subject technology. The advantages of the subject technology will be realized and attained by the structure particularly pointed out in the written description and claims hereof as well as the appended drawings.

It is to be understood that both the foregoing general description and the following detailed description are exemplary and explanatory and are intended to provide further explanation of the subject technology as claimed.

BRIEF DESCRIPTION OF THE DRAWINGS

The accompanying drawings, which are included to provide further understanding of the subject technology and are incorporated in and constitute a part of this description, illustrate aspects of the subject technology and, together with the specification, serve to explain principles of the subject technology.

FIGS. 1A-1D illustrate an example of a catheter according to some aspects of the subject technology.

FIGS. 2A-2D illustrate use of the catheter of FIGS. 1A-1D according to some aspects of the subject technology.

DETAILED DESCRIPTION

Figure 3A:
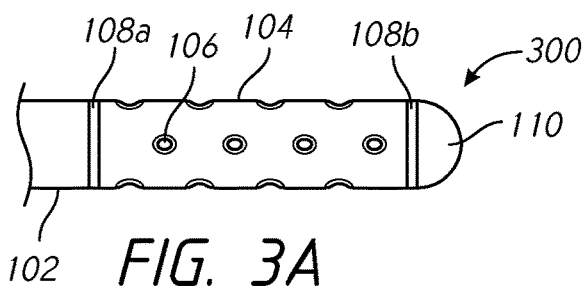
FIGS. 3A-3E illustrate an example of a catheter having a collapsible distal segment, and use of such catheter according to some aspects of the subject technology.

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, it will be clear and apparent to those skilled in the art that the subject technology is not limited to the specific details set forth herein and may be practiced using one or more implementations.

Devices are sometimes inserted into the vasculature to remove vascular debris (e.g., thrombi, emboli, foreign bodies). Such a device can include a distal portion or segment configured to capture vascular debris. Such a device can have a length sufficient to enable manipulation of the distal portion or segment positioned within the body of a patient using a proximal portion of the device at a location outside the body. Some techniques for removing vascular debris can utilize (concurrently or sequentially) such a device with additional medical devices, such as, for example, introducers, guidewires, and catheters (e.g., guide catheters and balloon catheters).

The subject technology relates to catheters for capturing and withdrawing vascular debris from a blood vessel. In some implementations of the subject technology, a catheter can have a distal segment with ports positioned along the length and around the circumference of the distal segment. The distal segment can be advanced into a thrombus, and positioned so that at least some of the ports are in the thrombus. When aspiration is applied through the ports, the thrombus can be pulled against the distal segment. In some implementations, portions of the thrombus can potentially be pulled into the ports. Port arrangement patterns, port shapes, and/or port sizes can vary among implementations. For example, the distal segment can include beveling of the external openings of the ports in some implementations. In some implementations, the ports can act as suction cups when aspiration is applied through a lumen extending through the catheter to the distal segment.

While thrombus is attached to an outside of the distal segment, the catheter can be withdrawn to remove captured thrombus from the patient. The catheter may be withdrawn a distance within the vessel distal of or outside an additional, larger catheter, and optionally may be retracted into the additional, larger catheter, such as a guide catheter or balloon catheter.

Although some implementations of the subject technology are disclosed herein with reference to thrombus and thrombectomy, the subject technology may be used to remove other forms of vascular debris compatible with one or more embodiments of the subject technology.

As used herein, the terms "treat," "treatment" and "treating" shall be given their ordinary meaning and shall refer to therapy, management, preventive care, repair, assessment, removal, and/or the like. With particular reference to stroke treatment, the terms can refer to the reduction or amelioration of the progression, severity, and/or duration of a stroke or a symptom thereof. Treatment as used herein with reference to stroke treatment includes, but is not limited to, decreasing the size or firmness of a clot, removing a clot, increasing blood flow, increasing cerebral perfusion, facilitating natural lysis of a clot, reducing destruction of brain synapses, improving modified Rankin scores, and improving brain function.

The term "removal" and its derivatives as used herein shall be given their ordinary meaning, and can refer to capture and extraction from a patient's body, or engagement and relocation of material, or portions of the material, to a different region of the body.

FIGS. 1A-1D illustrate an example of a catheter 100 according to some aspects of the subject technology. The catheter 100 of FIGS. 1A-1D comprises an elongate member 102, a distal end 110, a distal segment 104, and a lumen 112 extending through the elongate member to the distal segment 104.

The distal segment 104 of FIGS. 1A-1D can include an array of ports 106 positioned along a longitudinal length of the distal segment 104 and/or about a circumference of the distal segment 104. In one or more embodiments, the array of ports 106 is spaced evenly circumferentially around a longitudinal axis of the distal segment 104 and/or evenly longitudinally along the length of the distal segment 104. For example, the distance between adjacent ports, measured from the center of each port, can be the same in some embodiments. However, the longitudinal and/or circumferential port arrangement pattern for the array of ports 106 can vary among implementations.

The catheter 100 can include one or more markers, for example, as illustrated in FIGS. 1A and 1C. The catheter 100 of FIGS. 1A and 1C includes a proximal marker 108a and a distal marker 108b spaced from each other along the longitudinal length of the distal segment 104 of the elongate member 102. The markers 108a, 108b can extend completely around the circumference of the distal segment 104. In some embodiments, the marker(s) do not extend completely around the circumference of the distal segment 104. The proximal marker 108a, if present, can be spaced apart from the distal marker 108b, if present, by a distance equivalent to the longitudinal length of the distal segment 104. The distal marker 108b, if present, can be spaced from the distal end 110.

In some implementations, some or all of the port of the array of ports 106 have a segment, e.g. a radially outermost (or outer-surface-adjacent) segment, with a frusto-conical shape. In some implementations, the frusto-conical segment can extend the entire length of the port from the inner opening to the outer opening. As illustrated in FIG. 1D, for example, the port can have an outer opening that is larger than the inner opening. Where a port has a circular cross-sectional shape at the inner and outer openings, the outer opening can be greater in diameter than is the inner opening. In some embodiments, each port of the array of ports 106 can have a different port shape and/or port size from another port of the array. In some implementations, the ports function as suction cups when the aspiration is applied through the elongate member 102 to the distal segment 104. In some embodiments, some or all of the ports of the array of ports 106 are sized for aspiration of thrombus into the ports without aspirating thrombus into the lumen 112. The distal segment 104 can be formed, for example, of a polymer, plastic, metal or other material, or a combination thereof. The choice of material of the distal segment may be affected by the number of ports, port arrangement pattern, and/or collapsibility.

However, in some implementations the distal end 110 can have a shape that facilitates navigation of the vasculature, thrombus penetration, or both. In some implementations, the distal end 110 has a rounded shape, for example, as shown in FIGS. 1A and 1C. If present, a rounded distal end 110 can facilitate distal navigation of the catheter 100 without catching corners against a blood vessel wall.

The distal end 110 can be formed integrally with the distal segment 104 in some embodiments, or may be joined to the distal segment 104 after separate formation in other embodiments. The distal end 110 can be located adjacent to the distal segment 104.

The distal end 110 can provide stoppage for the aspiration applied through the distal segment 104. In some implementations, the distal end 110 is closed, for example, as shown in FIGS. 1A and 1C. In one or more implementations, the distal end 110 includes a hole sized to accommodate a guidewire extending therethrough. In some such embodiments, the distal end can be configured (e.g. with an annular or toroidal hemostatic seal) such that the hole self-seals when a guidewire is not extending therethrough. The distal end 110 can be formed, for example, of a polymer, plastic, metal or other material, or a combination thereof.

The elongate member 102 can include a proximal segment 103 (at a control end of the catheter 100) and the distal segment 104 (at an end of the elongate member 102 inserted into a patient's body). According to some embodiments, the length and diameter of the catheter 100 are suitable for inserting into a human patient and capable of reaching a target embolus in the region above the subclavian and common carotid arteries while still being accessible to a clinician from outside a patient's body. In some embodiments, the catheter 100 can have a total length from its proximal end to the distal end 110 of 100 cm to 200 cm (e.g., 100 cm, 130 cm, 150 cm, 180 cm, or 200 cm). In some embodiments, the distal segment 104 of the catheter 100 can have a total length of 10 mm to 40 mm (e.g., 10 mm, 15 mm, 20 mm, 25 mm, 30 mm, 35 mm, or 40 mm). In some embodiments, the distal segment 104 can have a maximum outer dimension (e.g., diameter) of 2 French (0.67 mm) to 3 French (1.0 mm). For example, the distal segment 104 can have a maximum outer dimension (e.g., diameter) of 2 French (0.67 mm), 2.4 French (0.8 mm), 2.6 French (0.87 mm), 2.8 French (0.93 mm), or 3 French (1.0 mm). In some embodiments, the distal segment 104 can have a maximum outer dimension (e.g., diameter) smaller than 2 French (0.67 mm) or larger than 3 French (1.0 mm).

FIG. 1B illustrates a cross-sectional view of the catheter 100 in FIG. 1A taken along an axis 1B-1B'. FIG. 1C illustrates a cross-sectional view of the catheter 100 in FIG. 1A taken along an axis 1C-1C', shown in FIGS. 1A and 1B. The distal segment 104 can comprise a tubular body having the array of ports 106 arranged around the circumference of the distal segment 104. As shown in FIGS. 1B and 1C, the array of ports 106 are in fluid communication with the lumen 112, such that the lumen 112 is in fluid communication with a space exterior to the catheter 100. The lumen 112 can extend from the proximal segment 103, e.g., from a location at or near the proximal end of the catheter 100, to the distal segment 104. Aspiration can be applied through the lumen 112 to array of ports 106.

As shown in FIG. 1D, one, some or all of the ports of the array 106 can comprise an outer segment 106a and an inner segment 106b. The outer segment 106a can have a frusto-conical shape. The frusto-conical shape may increase contact with and attachment between the distal segment 104 and thrombus. In some implementations, the inner segment 106b has a uniform cylindrical shape. In some implementations, the inner segment 106b can have a cylindrical shape having a diameter that is smaller than that of an outer opening 106c of the port. In some implementations, the entire length of the port from the outer opening 106c to the inner opening 106d can have a frusto-conical shape. In some embodiments, the outer opening 106c has a diameter that is 20%-50% (including, e.g., 20%, 30%, 40% or 50%) of the outside diameter of the distal segment 104. Separately or additionally, the outer opening 106c can have a diameter of 0.12 mm-1.5 mm, or 0.2 mm-1.0 mm (including, e.g., 0.12 mm, 0.2 mm, 0.5 mm, 0.8 mm, 1.0 mm, or 1.2 mm); however, diameters less than 0.12 mm or greater than 1.5 mm may be used in some embodiments. In some embodiments, the inner opening 106d has a diameter that is 25%-80% (including, e.g., 25%, 40%, 50%, 60% or 80%) of the diameter of the outer opening 106c. Separately or additionally, the inner opening 106d can have a diameter of 0.03 mm-1.2 mm, or 0.05 mm-0.8 mm (including, e.g., 0.03 mm, 0.1 mm, 0.3 mm, 0.5 mm, 0.8 mm, or 1.0 mm); however, diameters less than 0.03 mm or greater than 1.2 mm may be used in some embodiments. In some embodiments, the inner opening 106d, the outer opening 106c, or both are configured to inhibit movement of thrombus into the lumen 112 when aspiration is applied through the lumen to the ports. As shown in FIG. 1D, the inner segment 106b has a diameter equal to an inner diameter of the outer segment 106a. In some embodiments, the inner segment 106b can have a tapering shape extending from the inner opening 106d (at the inner wall of the distal segment 104) to the outer segment 106a.

FIGS. 2A-2D illustrate an example of a method of use of a catheter in a vasculature 202 (e.g., a blood vessel) for removing thrombus therefrom. FIG. 2A illustrates the catheter 100 extending through a larger catheter 204 (e.g., a guide or balloon catheter). FIG. 2B illustrates a thrombus 210 in the vasculature 202. The thrombus may be in contact with an inner wall of the vasculature 202.

FIG. 2A illustrates an embodiment of a system 200 for revascularization, clot management, and/or stroke treatment with the system positioned in the vasculature 202 (e.g., blood vessel). The revascularization system 200 includes the catheter 100 of FIGS. 1A-1D and another catheter 204, which is larger than the catheter 100. The catheter 204 can be a guide or balloon catheter, for example.

In some embodiments, the catheter 204 accesses a blood vessel under standard interventional procedures (e.g., using an endovascular or percutaneous approach via an incision in a femoral artery and/or using the Seldinger technique). The catheter 204 can be used to guide the elongate member 102 in some embodiments. In some embodiments, the elongate member 102 of the catheter 100 can be inserted within the catheter 204 and advanced to a distal end of the catheter 204. The catheter 204 can have an inner diameter large enough to receive the catheter 100 and still allow for contrast injection while the catheter 100 is in place, thereby advantageously allowing for fluoroscopic visualization during the procedures. In some embodiments, the catheter 204 includes a balloon catheter configured to temporarily obstruct blood flow during removal of vascular debris. In some embodiments, the catheter 204 is aspirated (e.g., with a syringe) during retraction of the catheter 100 into the catheter 204 for removal of vascular debris. According to some embodiments, the length and diameter of the catheter 204 are suitable for inserting into a human patient and capable of reaching a target embolus in the region above the subclavian and common carotid arteries while still being accessible to a clinician from outside a patient's body. The guide catheter 204 can comprise or include a neurovascular guide catheter, and can have a length of 100 cm to 200 cm (e.g., 100 cm, 130 cm, 150 cm, 180 cm, or 200 cm) and longer than the length of the catheter 100. In some embodiments, the system 200 can include a neurovascular access catheter configured to be inserted within the catheter 204, and to receive insertion of the catheter 100 therein.

The catheter 100 can be configured to be deployed over one or more guidewires. In some embodiments, the catheter 100 and catheter 204 are advanced over the one or more guidewires toward the location of the clot; however, in other embodiments, only the catheter 100 is advanced over a guidewire. In some embodiments, the elongate member 102 of the catheter 100 includes a guidewire lumen configured to receive the guidewire. The guidewire can stay in place within the catheter 100 or removed during aspiration. The guidewire advantageously can be left in place to maintain access to a target location when multiple devices are inserted and removed in succession during a treatment procedure. In some embodiments, the distal end 110 of the catheter 100 is closed, and does not have any opening for a guidewire.

FIG. 2B shows a distal segment 104 positioned proximate and proximal to the thrombus 210 within the vasculature 202. If the catheter 204 is present and has been used to facilitate delivery of the catheter 100 to the illustrated location, the distal segment 104 shown in FIG. 2B has been moved distally outside of a distal opening of the catheter 204.

In one or more implementations, the elongate member 102 is configured to manipulate the distal segment 104 positioned within the body of a patient using the proximal segment 103 at a location outside of the body. A distal or proximal motion of the elongate member 102 is generally initiated by a user who can controllably operate the elongate member 102 at the proximal end (FIG. 2A).

As shown in FIG. 2C, the catheter 100 can be positioned at a target location within the vasculature 202 and to engage a thrombus 210. As shown in FIG. 2C, the distal segment 104 is positioned in contact with the thrombus 210 in the vasculature 202. In positioning the distal segment 104 in contact with the thrombus 210, the distal segment 104 can be positioned through the thrombus 210 such that at least some ports of the array of ports 106 are in the thrombus 210. The distal segment 104 can be positioned such that the thrombus 210 covers at least a portion of the array of ports 106 in some implementations, or covers the array of ports 106 in its entirety in other implementations. In some implementations, all of the ports of the array of ports 106 are positioned within the thrombus 210. If the distal end 110 has a rounded shape, the rounded shape can facilitate piercing of and passage through the thrombus 210 by the distal segment 104. The distal end 110 can be positioned within the thrombus 210 in some implementations, or moved beyond (distal to) the thrombus 210 in other implementations.

In some implementations, aspiration is applied through the array of ports 106 while the distal segment 104 is in contact with the thrombus 210. In some implementations, aspiration is applied through the array of ports 106 while at least some ports of the array are in contact with the thrombus 210. In some implementations, aspiration is applied through the array of ports 106 while all of the ports of the array are in contact with the thrombus 210. In some implementations, aspiration through the ports can pull the thrombus 210 toward the distal segment 104, into the ports of the array 106, into the lumen 112, or a combination thereof. When the thrombus 210 is in contact with the outer surface of the distal segment 104, portions of the thrombus can be aspirated into some or all of the ports of the array 106 in some implementations. For example, the thrombus 210 can fill the outer openings 106c (FIG. 1D) of the ports in their entirety while filling some or all of the length of the ports (e.g., some or all of the lengths of the outer segment 106a, and inner segment 106b) In this respect, the beveling or tapering of the ports, if present, may increase contact between the distal segment 104 and the thrombus 210. In some implementations, the thrombus 210 can partially fill the outer openings 106c (FIG. 1D) of the ports. When the thrombus 210 is in contact with the outer surface of the distal segment 104, portions of the thrombus can be aspirated into the lumen 112 of the catheter 100 in some implementations. In some such implementations, portions of the thrombus can be aspirated into the lumen 112 of the catheter 100 without preventing further aspiration through ports of the array 106 located distal thereto.

FIG. 2D shows the catheter 100 being retracted, with the distal segment 104 moving proximally toward the catheter 204 while attached to the thrombus 210. The catheter 100 is retracted with at least a portion of the thrombus 210 on an exterior of the distal segment 104, to remove the thrombus 210 from the vasculature 202 (e.g., blood vessel). In some implementations, the majority of the thrombus 210 is attached to the catheter 100 and disposed exterior to distal segment 104 for removal from the vasculature. In some implementations, the proportion of the thrombus 210 attached to the catheter 100 and disposed exterior to distal segment 104 for removal from the vasculature is between 50% and 100%. In some implementations, the proportion of the thrombus 210 attached to the catheter 100 and disposed exterior to distal segment 104 for removal from the vasculature is greater than 25%.

In withdrawing the catheter 100 from the vasculature 202, the catheter 100 can be retracted into another catheter (e.g., the guide catheter 204 or a different catheter) with the thrombus 210 at least partially on an exterior of the distal segment 104. The catheter 100 can be withdrawn a distance within the vasculature (e.g., blood vessel) outside the additional catheter before retracting the catheter 100 into the additional catheter (e.g., the guide catheter 204 or a different catheter). For example, the catheter 100 can be withdrawn within the vasculature 3 cm to 24 cm outside the guide catheter 204 while the distal segment 104 is attached to the thrombus 210 for removal. As part of the withdrawing, at least a portion of the thrombus 210 adhered to the distal segment 104 is removed from the inner wall of the vasculature 202 while aspiration is applied through the array of ports 106. In some implementations, a residue portion 211 may remain on the inner wall. In some aspects, at least a portion of the thrombus 210 is positioned into at least a portion of the array of ports 106 while aspiration is applied and the catheter 100 is refracted. In some implementations, proximal motion of the distal segment 104 with a majority of the thrombus 210 on the exterior of the distal segment 104 can effectively retrieve the thrombus 210 from the vasculature (e.g., into the guide catheter 204).

FIGS. 3A-3E illustrate an example of a catheter 300 according to some aspects of the subject technology. The catheter 300 can, in some embodiments, be similar in structure, function and/or method of use to the catheter 100, while incorporating any one or more of the difference(s) that are described herein. Therefore, the same reference numerals are used with reference to corresponding features of the catheter 300, and a detailed description of such features of the catheter 300 is not repeated with reference to catheter 300.

As shown in FIG. 3A, the catheter 300 can comprise an elongate member 102, a distal end 110, and a distal segment 104. The catheter 300 also has a lumen 112 extending to the distal segment 104. The distal segment 104 of the catheter 300 has a non-collapsed configuration, shown for example in FIG. 3A, and a collapsed configuration, shown for example in FIG. 3B. In the collapsed configuration some or all of the length of the distal segment 104 collapses inwardly, reducing the volume of the distal segment and allowing additional volume for thrombus. The distal segment 104 transitions from the non-collapsed configuration to the collapsed configuration when aspiration is applied through the lumen 112 of the catheter 300. In some implementations, the distal segment transitions from the non-collapsed configuration to the collapsed configuration when aspiration is applied through the lumen 112 of the catheter 300 only while at least some or all of the ports of the array 106 are covered by thrombus. In some implementations, the distal segment transitions from the non-collapsed configuration to the collapsed configuration when aspiration is applied through the lumen 112 of the catheter 300 only when all of the ports of the array 106 are covered by thrombus. In some implementations, the distal segment transitions from the non-collapsed configuration to the collapsed configuration when aspiration is applied through the lumen 112 of the catheter 300 regardless of whether any ports of the array 106 are covered by thrombus.

Figure 3B:
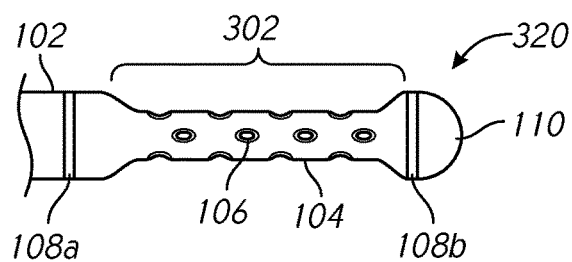

As shown in FIG. 3B, a section 302 of the distal segment 104 that includes at least some of the array of ports 106 collapses inwardly when aspiration is applied through the lumen 112. In some embodiments having a collapsible distal segment 104, the distal end 110 is not collapsible (e.g., under use aspiration pressures). For example, the distal end 110 can be formed, for example, of a polymer, plastic, metal or other material, or a combination thereof. The materials and construction of the distal end 110 can be sufficiently rigid that the distal end 110 retains its shape during aspiration.

In some embodiments, the distal segment 104 can have a non-collapsed maximum outer dimension (e.g., diameter) of 2 French (0.67 mm) to 3 French (1.0 mm). For example, the distal segment 104 can have a maximum non-collapsed outer dimension (e.g., diameter) of 2 French (0.67 mm), 2.4 French (0.8 mm), 2.6 French (0.87 mm), 2.8 French (0.93 mm), or 3 French (1.0 mm). In some embodiments, the distal segment 104 can have a non-collapsed maximum outer dimension (e.g., diameter) smaller than 2 French (0.67 mm) or larger than 3 French (1.0 mm). The collapsed section 302 can have a collapsed maximum outer dimension (e.g., diameter) that is less than the non-collapsed maximum outer dimension (e.g., diameter) of the distal segment 104. In some embodiments, the collapsed maximum outer dimension is 90% or less of the non-collapsed maximum outer dimension. In some embodiments, the collapsed maximum outer dimension is 75% or less of the non-collapsed maximum outer dimension.

In some implementations, the lumen 112 can retain a passage that still allows for aspiration when the distal segment is in a collapsed configuration. In some embodiments, the ability to aspirate through the lumen 112 can be diminished in the collapsed configuration.

Figure 3C:
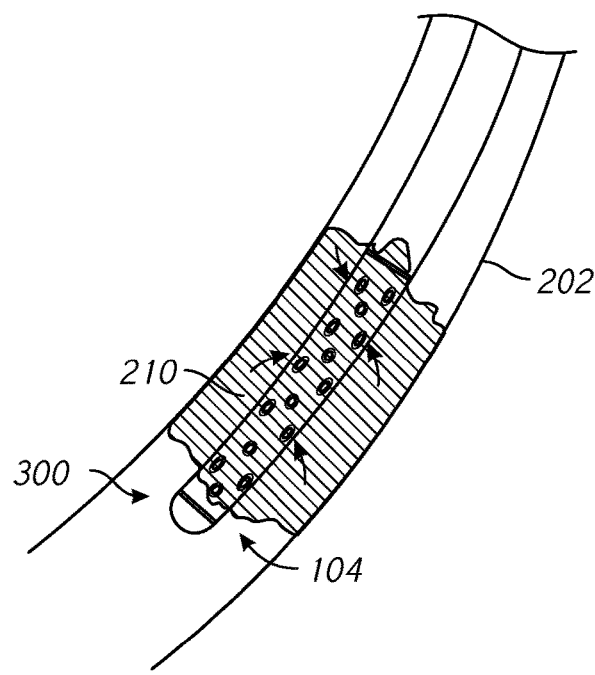
Figure 3D:
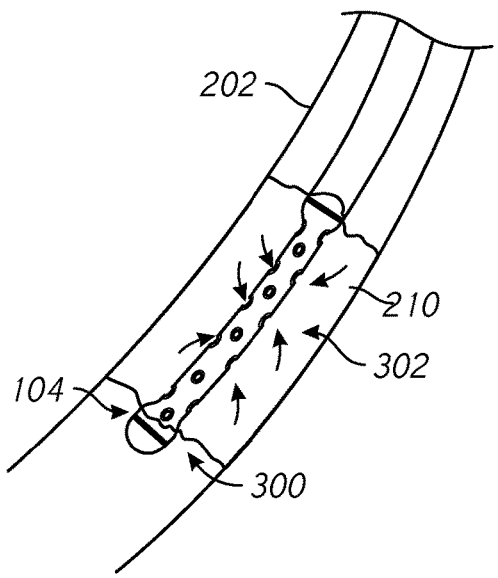
Figure 3E:
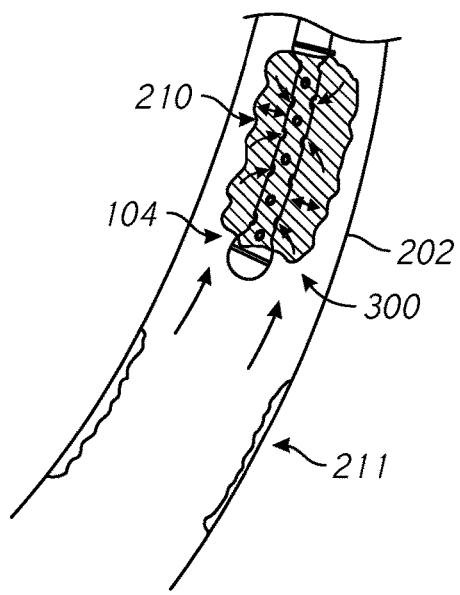

FIGS. 3C-3E illustrate an example of a method of use of a catheter in a vasculature 202 (e.g., a blood vessel) for removing thrombus thereforefrom. In some embodiments, the method of FIGS. 3C-3E can be similar to the method(s) of FIGS. 2A-2D, while incorporating any one or more of the difference(s) that are described herein. FIG. 3C illustrates a thrombus 210 in the vasculature 202 and the catheter 300 positioned in contact with the thrombus 210. The catheter 300 can be positioned in the vasculature proximate the thrombus 210, and positioned in the thrombus 210 as described with reference to FIGS. 2A-2C. The thrombus 210 may be in contact with an inner wall of the vasculature 202.

As shown in FIG. 3C, the catheter 300 can be positioned at a target location within the vasculature 202 and to engage the thrombus 210. As shown in FIG. 3C, the distal segment 104 is positioned in contact with the thrombus 210 in the vasculature 202, with the distal segment in a non-collapsed configuration.

Aspiration can be applied through the array of ports 106 while the distal segment 104 of the catheter 300 is in contact with the thrombus 210. Application of aspiration through the array of ports 106 while the distal segment 104 of the catheter 300 is in contact with the thrombus 210 can modify the distal segment 104 to a collapsed configuration, as discussed above. FIG. 3D illustrates the distal segment 104 of the catheter 300 in such a collapsed configuration. In some implementations, aspiration modifies the distal segment 104 to a collapsed configuration only if at least some ports of the array are in contact with the thrombus 210. For example, the section 302 of the distal segment 104 collapses when a number of ports covered by thrombus reaches a threshold. In some implementations, aspiration modifies the distal segment 104 to a collapsed configuration only if all of the ports of the array are in contact with the thrombus 210. In some implementations, aspiration modifies the distal segment 104 to a collapsed configuration regardless of whether any ports of the array are in contact with the thrombus 210. In some implementations, collapse of the distal segment 104 can detach some or all the thrombus 210 from the inner wall of the vasculature, potentially leaving behind a residue portion 211.

FIG. 3E shows the catheter 300 being retracted, with the distal segment 104 moving proximally toward the catheter 204 while attached to the thrombus 210. The catheter 300 is retracted with at least a portion of the thrombus 210 on an exterior of the distal segment 104, to remove the thrombus 210 from the vasculature 202 (e.g., blood vessel). In withdrawing the catheter 300 from the vasculature 202, the catheter 300 can be retracted into another catheter (e.g., the guide catheter 204 or a different catheter) with the thrombus 210 at least partially on an exterior of the distal segment 104. The catheter 300 can be withdrawn a distance within the vasculature (e.g., blood vessel) outside the additional catheter before retracting the catheter 300 into the additional catheter (e.g., the guide catheter 204 or a different catheter), as discussed in greater detail above.

FIGS. 4A-4D illustrate an example of a catheter 400 according to some aspects of the subject technology. The catheter 400 can, in some embodiments, be similar in structure, function and/or method of use to the catheter 100 or the catheter 300, while incorporating any one or more of the difference(s) that are described herein. Therefore, the same reference numerals are used with reference to corresponding features of the catheter 400, and a detailed description of such features of the catheter 400 is not repeated with reference to catheter 400.

Figure 4A:
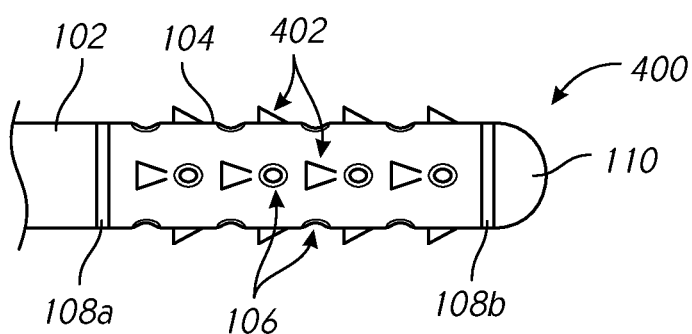
FIG. 4A-4D illustrate an example of a catheter having a plurality of projections, and use of such catheter according to some aspects of the subject technology.

As shown in FIG. 4A, the catheter 400 comprises an elongate member 102, a distal end 110, and a distal segment 104. The catheter 400 also has a lumen 112 extending to the distal segment 104. As shown in FIG. 4A, the catheter 400 comprises projections 402 disposed along and around the distal segment 104. In some embodiments, the projections include a plurality of projections 402 equally longitudinally spaced and circumferentially arranged around a longitudinal axis of the distal segment 104. Some or all of the projections 402 can be configured to slide distally through a thrombus within a blood vessel and to pull the thrombus when the elongate member 102 is retracted proximally.

In some implementations, some or all of the projections 402 include a distal surface and a proximal surface. The distal surface and the proximal surface each can have a slope relative to a longitudinal axis of the distal segment 104, where the slope of the distal surface is less than the slope of the proximal surface. For example, the set of projections 402 can have distal surfaces sloping downward toward the distal end 110 and proximal surfaces with slopes greater than that of the distal surfaces. The slope of the proximal surface can be 45° or greater, 60° or greater, 75° or greater, or 90° or greater. The slope of the distal surface can be 45° or less, 30° or less, or 15° or less.

Figure 4B:
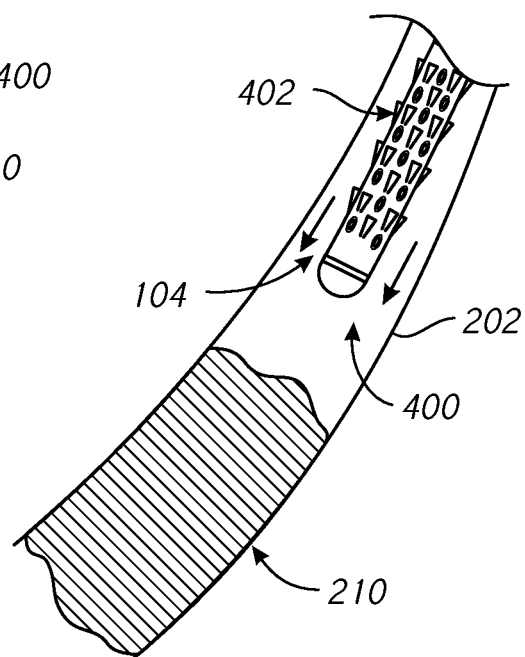
Figure 4C:
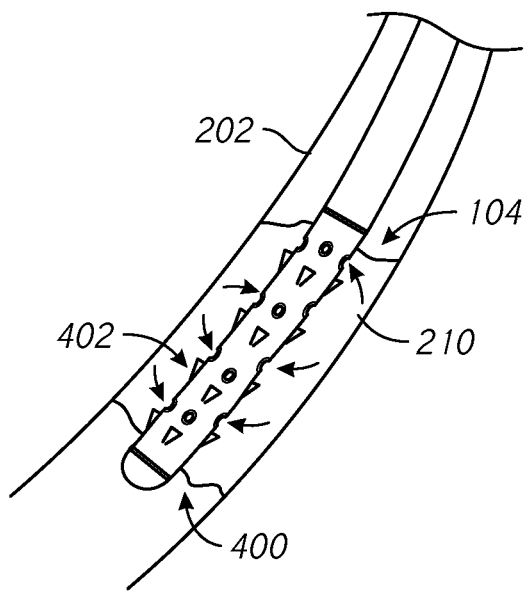
Figure 4D:
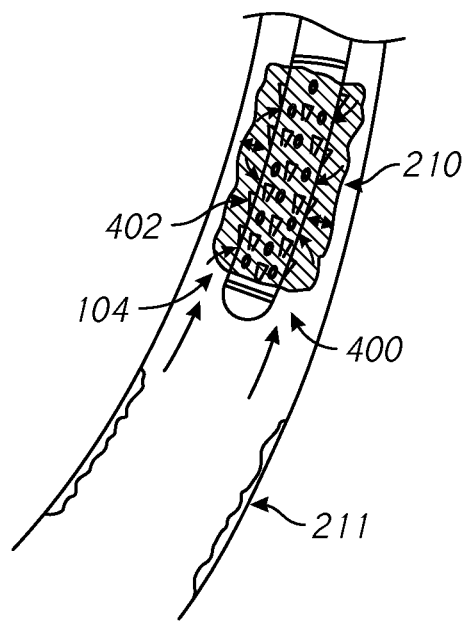

FIGS. 4B-4D illustrate an example of use of a catheter in a vasculature 202 (e.g., a blood vessel) for removing thrombus thereforefrom. FIG. 4B illustrates a thrombus 210 in the vasculature 202 and the catheter 400 positioned in contact with the thrombus 210. FIG. 4B shows the distal segment 104 of the catheter 400 positioned proximate and proximal to the thrombus 210 within the vasculature 202. The catheter 400 can be positioned in the vasculature proximate the thrombus 210 as described with reference to FIGS. 2A-2C. The thrombus 210 may be in contact with an inner wall of the vasculature 202.

As shown in FIG. 4C, the catheter 400 can be positioned at a target location within the vasculature 202 and to engage the thrombus 210. As discussed above, some or all of the ports of the array 106 can be positioned in contact with the thrombus 210. As shown in FIG. 4C, some or all of the radially outwardly extending projections 402 can be positioned in contact with the thrombus 210 in the vasculature 202. The slope of the distal surfaces of the projections can facilitate the distal segment 104 sliding distally into the thrombus 210. As discussed above, aspiration is applied through the array of ports 106 while the distal segment 104 of the catheter 300 is in contact with the thrombus 210. In some implementations, a distal segment 104 having projections 402 can be configured as discussed above such that application of aspiration modifies the distal segment from a non-collapsed configuration to a collapsed configuration.

FIG. 4D shows the catheter 400 being retracted, with the distal segment 104 moving proximally toward the catheter 204 while attached to the thrombus 210. As the catheter 400 is retracted, the slope of the proximal surfaces of the projections 402 can facilitate pulling the thrombus 210 in a proximal direction. The catheter 400 is retracted with at least a portion of the thrombus 210 on an exterior of the distal segment 104, to remove the thrombus 210 from the vasculature 202 (e.g., blood vessel). In withdrawing the catheter 400 from the vasculature 202, the catheter 400 can be retracted into another catheter (e.g., the guide catheter 204 or a different catheter) with the thrombus 210 at least partially on an exterior of the distal segment 104. The catheter 400 can be withdrawn a distance within the vasculature (e.g., blood vessel) outside the additional catheter before retracting the catheter 400 into the additional catheter (e.g., the guide catheter 204 or a different catheter), as discussed in greater detail above.

FIGS. 5A-5D illustrate an example of a catheter 500 according to some aspects of the subject technology. The catheter 500 can, in some embodiments, be similar in structure, function and/or method of use to the catheter 100, the catheter 300, or the catheter 400, while incorporating any one or more of the difference(s) that are described herein. Therefore, the same reference numerals are used with reference to corresponding features of the catheter 500, and a detailed description of such features of the catheter 500 is not repeated with reference to catheter 500.

Figure 5A:
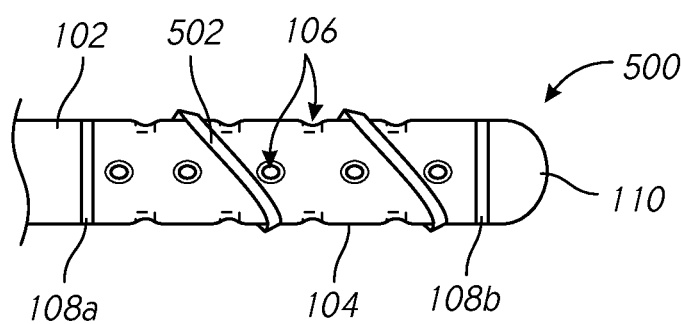
FIG. 5A-5D illustrate an example of a catheter having a spiral projection, and use of such catheter according to some aspects of the subject technology.

As shown in FIG. 5A, the catheter 500 comprises an elongate member 102, a distal end 110, and a distal segment 104. The catheter 500 also has a lumen 112 extending to the distal segment 104. As shown in FIG. 5A, the catheter 500 comprises one or more projections 502 disposed along and around the distal segment 104. In some embodiments, some or all of the projections 502 can form ridges spiraling along and around a longitudinal axis of the distal segment 104. In some embodiments, the projections 502 include a plurality of projections 502 equally spaced and circumferentially arranged around a longitudinal axis of the distal segment 104. In some implementations, some or all of the projections 502 can be configured to slide distally through a thrombus within a blood vessel and to pull the thrombus when the elongate member 102 is retracted proximally. In some implementations, the projections 502 are configured to screw distally into a thrombus 210 within the vasculature and to pull the thrombus when the catheter 500 is retracted proximally. In some implementations, a catheter can comprise a combination of the projections 402 disclosed with reference to FIGS. 4A-4D and the projections 502 disclosed with reference to FIGS. 5A-5D.

In some implementations, some or all of the projections 502 each include a distal surface and a proximal surface. The distal surface and the proximal surface each can have a slope relative to a longitudinal axis of the distal segment 104, where the slope of the distal surface is less than the slope of the proximal surface. For example, the set of projections 502 can have distal surfaces sloping downward toward the distal end 110 and proximal surfaces with slopes greater than that of the distal surfaces. The slope of the proximal surface can be 45° or greater, 60° or greater, 75° or greater, or 90° or greater. The slope of the distal surface can be 45° or less, 30° or less, or 15° or less.

Figure 5B:
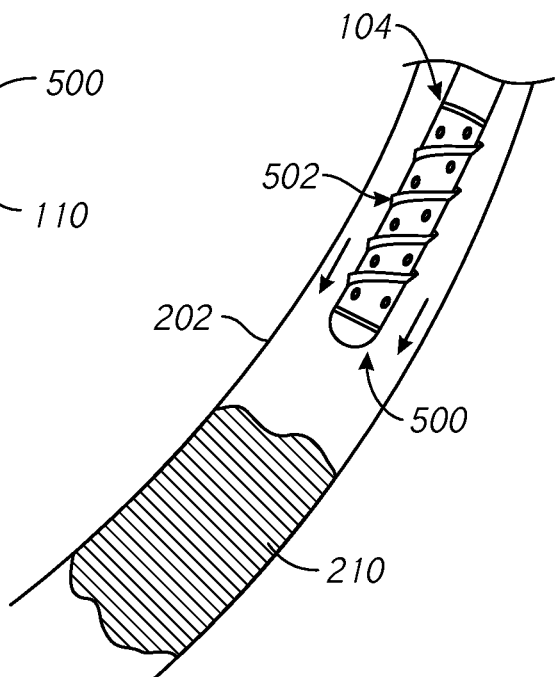
Figure 5C:
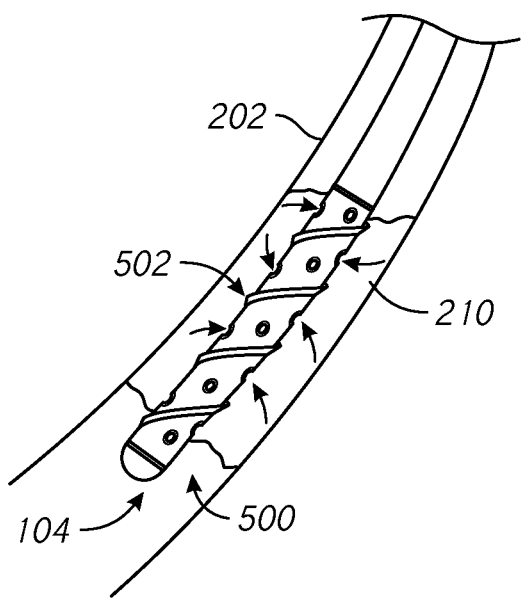
Figure 5D:
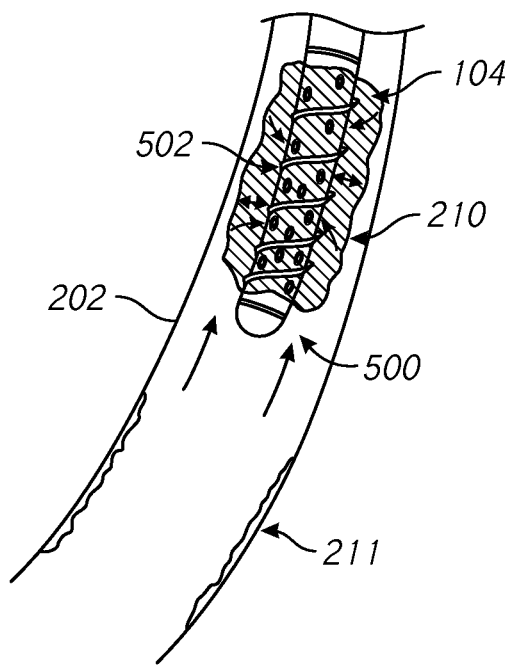

FIGS. 5B-5D illustrate an example of use of a catheter in a vasculature 202 (e.g., a blood vessel) for removing thrombus therefrom. FIG. 5B illustrates a thrombus 210 in the vasculature 202 and the catheter 500 positioned in contact with the thrombus 210. FIG. 5B shows the distal segment 104 of the catheter 500 positioned proximate and proximal to the thrombus 210 within the vasculature 202. The catheter 500 can be positioned in the vasculature proximate the thrombus 210 as described with reference to FIGS. 2A-2C. The thrombus 210 may be in contact with an inner wall of the vasculature 202.

As shown in FIG. 5C, the catheter 500 can be positioned at a target location within the vasculature 202 and to engage the thrombus 210. As discussed above, some or all of the ports of the array 106 can be positioned in contact with the thrombus 210. As shown in FIG. 5C, some or all of the radially outwardly extending projections 502 can be positioned in contact with the thrombus 210 in the vasculature 202. The slope of the distal surfaces of the projections can facilitate the distal segment 104 sliding distally into the thrombus 210. Additionally or alternatively, the distal segment 104 comprising the projections 502 can be screwed distally into the thrombus 210. As discussed above, aspiration is applied through the array of ports 106 while the distal segment 104 of the catheter 300 is in contact with the thrombus 210. In some implementations, a distal segment 104 having projections 502 can be configured as discussed above such that application of aspiration modifies the distal segment from a non-collapsed configuration to a collapsed configuration.

FIG. 5D shows the catheter 500 being retracted, with the distal segment 104 moving proximally toward the catheter 204 while attached to the thrombus 210. As the catheter 500 is retracted, the slope of the proximal surfaces of the projections 502 can facilitate pulling the thrombus 210 in a proximal direction. The catheter 500 is retracted with at least a portion of the thrombus 210 on an exterior of the distal segment 104, to remove the thrombus 210 from the vasculature 202 (e.g., blood vessel). In withdrawing the catheter 500 from the vasculature 202, the catheter 500 can be retracted into another catheter (e.g., the guide catheter 204 or a different catheter) with the thrombus 210 at least partially on an exterior of the distal segment 104. The catheter 500 can be withdrawn a distance within the vasculature (e.g., blood vessel) outside the additional catheter before retracting the catheter 500 into the additional catheter (e.g., the guide catheter 204 or a different catheter), as discussed in greater detail above.

Phrases such as an aspect, the aspect, another aspect, some aspects, one or more aspects, an implementation, the implementation, another implementation, some implementations, one or more implementations, an embodiment, the embodiment, another embodiment, some embodiments, one or more embodiments, a configuration, the configuration, another configuration, some configurations, one or more configurations, the subject technology, the disclosure, the present disclosure, other variations thereof and alike are for convenience and do not imply that a disclosure relating to such phrase(s) is essential to the subject technology or that such disclosure applies to all configurations of the subject technology. A disclosure relating to such phrase(s) can apply to all configurations, or one or more configurations. Such disclosure can provide one or more examples. A phrase such as an aspect can refer to one or more aspects and vice versa, and this applies similarly to other phrases.

Any implementation described herein as an "example" is not necessarily to be construed as preferred or advantageous over other implementations. Furthermore, to the extent that the term "include," "have," or the like is used in the description or the claims, such term is intended to be inclusive in a manner similar to the term "comprise" as "comprise" is interpreted when employed as a transitional word in a claim.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for."

The previous description is provided to enable any person skilled in the art to practice the various aspects described herein. Various modifications to these aspects will be readily apparent to those skilled in the art, and the generic principles defined herein can be applied to other aspects. Thus, the claims are not intended to be limited to the aspects shown herein, but are to be accorded the full scope consistent with the language claims, wherein reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the subject disclosure.

What is claimed is:

1. An aspiration catheter comprising: an elongate member comprising a distal end, a distal segment, and a lumen extending to the distal segment, the distal end being closed, the distal segment comprising a unitary tubular sidewall having an array of ports extending through the sidewall, the array of ports positioned along a longitudinal length of the distal segment and about a circumference of the distal segment, the array of ports being in fluid communication with the lumen, wherein at least a portion of the tubular sidewall that includes at least some of the array of ports is collapsible when aspiration is applied through the lumen, wherein each port of the array of ports has an inner opening that is smaller than an outer opening of the port.

2. The aspiration catheter of claim 1, wherein the array of ports are configured to inhibit movement of a thrombus into the lumen when aspiration is applied through the lumen to the ports.

3. The aspiration catheter of claim 1, wherein the distal end has a rounded shape.

4. The aspiration catheter of claim 1, wherein the array of ports are spaced evenly around a longitudinal axis of the distal segment.

5. An aspiration catheter comprising: an elongate member comprising a distal end, a distal segment, and a lumen extending to the distal segment, the distal end being closed, the distal segment comprising a unitary tubular sidewall having an array of ports extending through the sidewall, the array of ports positioned along a longitudinal length of the distal segment and about a circumference of the distal segment, the array of ports being in fluid communication with the lumen, wherein at least a portion of the tubular sidewall that includes at least some of the array of ports is collapsible when aspiration is applied through the lumen, wherein the distal segment comprises one or more projections disposed along and around the tubular sidewall, the one or more projections projecting radially outwardly from the tubular sidewall, wherein each of the one or more projections is configured to slide distally through a thrombus within a blood vessel and to pull the thrombus when the elongate member is retracted proximally, wherein each of the one or more projections comprises a distal surface and a proximal surface, the distal surface and the proximal surface each having a slope relative to a longitudinal axis of the distal segment, and the slope of the distal surface being less than the slope of the proximal surface.

6. An aspiration catheter comprising: an elongate member comprising a distal end, a distal segment, and a lumen extending to the distal segment, the distal end being closed, the distal segment comprising a unitary tubular sidewall having an array of ports extending through the sidewall, the array of ports positioned along a longitudinal length of the distal segment and about a circumference of the distal segment, the array of ports being in fluid communication with the lumen, wherein at least a portion of the tubular sidewall that includes at least some of the array of ports is collapsible when aspiration is applied through the lumen, wherein the distal segment comprises one or more projections disposed along and around the tubular sidewall, the one or more projections projecting radially outwardly from the tubular sidewall, wherein at least one projection spirals along and around the distal segment of the elongate member.

7. The aspiration catheter of claim 6, wherein each spiraling projection comprises a distal surface and a proximal surface, the distal surface and the proximal surface each having a slope relative to a longitudinal axis of the distal segment, the slope of the distal surface being less than the slope of the proximal surface.

* * * * *